(12) United States Patent
Obaje

(10) Patent No.: US 6,846,916 B2
(45) Date of Patent: Jan. 25, 2005

(54) TRANS-ACIDOLYSIS PROCESS FOR THE PREPARATION OF CARBOHYDRATE FATTY-ACID ESTERS

(75) Inventor: Olobo Jonathan Obaje, Singapore (SG)

(73) Assignee: URAH Resources (Nigeria) Ltd., Ayangba (NG)

( * ) Notice: Subject to any disclaimer, the term of this patent is extended or adjusted under 35 U.S.C. 154(b) by 20 days.

(21) Appl. No.: 10/050,402

(22) Filed: Jan. 15, 2002

(65) Prior Publication Data

US 2002/0120133 A1 Aug. 29, 2002

(30) Foreign Application Priority Data

Feb. 24, 2001 (SG) ...................................... 200100727-7

(51) Int. Cl.[7] .......................... C07G 3/00; C07H 15/00; C07H 17/00
(52) U.S. Cl. ..................... 536/18.6; 536/18.5; 536/115; 536/116; 536/119; 536/120; 536/124
(58) Field of Search ............................... 536/18.5, 18.6, 536/115, 116, 119, 120, 124

(56) References Cited

U.S. PATENT DOCUMENTS

| | | | | |
|---|---|---|---|---|
| 3,054,789 A | * | 9/1962 | D'Amato | |
| 3,951,945 A | * | 4/1976 | Heesen et al. | 260/210 |
| 3,956,278 A | | 5/1976 | Prey | 260/234 |
| 4,327,183 A | * | 4/1982 | Masuda et al. | 435/274 |
| 5,008,387 A | * | 4/1991 | Matsumoto et al. | 536/119 |
| 5,440,027 A | * | 8/1995 | Hasenhuettl | 536/115 |
| 5,596,085 A | * | 1/1997 | Silver et al. | 536/18.6 |
| 5,908,922 A | | 6/1999 | Kasori et al. | 536/18.6 |
| 5,945,519 A | | 8/1999 | Desai et al. | 536/18.6 |

FOREIGN PATENT DOCUMENTS

| | | | |
|---|---|---|---|
| DD | DD227137 | 9/1985 | ........... C07H/13/06 |
| EP | 0062565 | 10/1982 | ........... C07H/13/06 |
| EP | 0647652 | 4/1995 | ........... C07H/3/00 |
| EP | 0647653 | 4/1995 | ........... C07H/3/00 |

* cited by examiner

Primary Examiner—James O. Wilson
Assistant Examiner—Patrick Lewis
(74) Attorney, Agent, or Firm—Nath & Associates PLLC; Harold L. Novick; Joshua B. Goldberg

(57) ABSTRACT

The present invention relates to a low temperature, solvent-free trans-acidolysis process for preparing surface-active carbohydrate fatty-acid esters comprising the steps of:

(e) reacting acylated carbohydrate with free fatty acid in the presence of acid catalyst, under reduced pressure, and without adding any solvent;

(f) decolorizing and separating the reaction mixture obtained in step (a) into unreacted fatty acid layer and a carbohydrate fatty-ester layer;

(g) precipitating out the unreacted acylated carbohydrate;

(h) librating the hydroxyl groups by partial hydrolysis in the presence of an acid catalyst;

(i) removing the unreacted free fatty acids and unreacted carbohydrate esters of low molecular-weight carboxylic acids during purification, and recycling the removed unreacted free fatty acids and carbohydrate esters to the starting reactant mixture.

18 Claims, 2 Drawing Sheets

TRANS-ACIDOLYSIS PROCESS FOR THE PREPARATION OF CARBOHYDRATE FATTY-ACID ESTERS

BACKGROUND OF THE INVENTION (a) Field of the Invention

The present invention relates to process for production of surface-active carbohydrate fatty-acid esters, in particular, a low temperature, solvent-free trans-acidolysis reaction between carbohydrate ester of low molecular-weight carboxylic acid and free fatty acid under reduced pressure and in the present of acid catalyst.

(b) Description of the Prior Art

Carbohydrate fatty-acid esters are non-irritant, nonionic surfactants with excellent biodegradability properties. They are used to solubilize membrane proteins and to formulate many grades of detergents, pharmaceutical, food and cosmetic products. Carbohydrate fatty-acid esters are also used as therapeutic agents. U.S. Pat. No. 5,739,117, Yokoyama and Yoneda, issued April 1998, describe the use of glucose esters as cerebral metabolism improving agent. Carbohydrate esters can also be used for treating gallstones (U.S. Pat. No. 4,264,583), colonic disorders (U.S. Pat. No. 5,840,860) and hypercholesterolemia (U.S. Pat. No. 4,241,054). They are also known to exhibit anti-microbial and insecticidal activities. But the synthetic methods for carbohydrates fatty-acid esters are faced with many limitations.

Processes for the synthesis of sucrose fatty acid esters in solvent and non-solvent environments; following batch-wise or continuous reaction regimes currently exist. Prior art is described in U.S. Pat. Nos. 4,614,718, 4,927,920; 4,966,966; 4,968,791; 4,996,309; 5,043,438; and 5,908,922. The conventional methods, described in the prior, art for producing carbohydrate fatty esters have however encountered the following disadvantages and limitations:

(1) The transesterification method, currently favoured by most industrial producers of carbohydrate fatty esters, is a reversible process with poor conversion equilibria because the substrate sugars and fatty acid moieties are immiscible due to polarity differences. Thus, low product yield characterize the processes;

(2) Finding mutual solvent with good safety credentials. Mutual solvents, such as pyridine, N, N-dimethylformamide (DMF), dimethylacetamide (DMA), dimethylsulfoxide (DMSO), chloroform, benzene and toluene, are required to solubilize the substrates. These mutual solvents are toxic and cannot be removed to the level compatible with current regulations, thus limiting product applications.

(3) Complex and costly product purification procedures.

(4) Thermal degradation and isomerization of the reactant carbohydrate at temperatures above 100 degree C., which is normally required in most known processes.

(5) High catalyst load, especially in enzymatic processes.

U.S. Pat. No. 5,945,519 describes a process for the solvent-free preparation of sucrose fatty acid esters and their mixtures with nonsugar polyol fatty acid esters. In this process, a sucrose is reacted with one or more fatty acid alkyl esters of a chain length of 6 to 20 carbon atoms at temperatures between 120 to 160 degree C. and the reaction mixture is then reacted at reduced pressure with fatty acid alkyl ester, and then filtered without addition of solvent.

To address the problem associated with the use of toxic mutual solvents, U.S. Pat. No. 4,996,309 discloses a process for preparing sucrose fatty acid esters by reacting sucrose and a fatty acid alkyl ester in an aqueous reaction system in the presence of an alkaline catalyst. The catalyst introduces large amounts of soap in the product. Separation and purification is thus made cumbersome and expensive, involving a reverse osmosis and an ultrafiltration step. Even then, only 70% product purity is normally attainable.

U.S. Pat. No. 5,872,245 describe a continuous process for the synthesis of sucrose fatty acid esters by reacting sucrose in limited amount of methanol, as "carrier" solvent, with fatty acid methyl ester in the presence of stationary trans-esterification catalyst and mechanical emulsification. The process employs heavy metal catalysts, such as Zn, Cu, Sn and Pb, in addition to catalytic amount of sodium hydroxide. Product separation is achieved by density differentiations.

The process does not however address the color and antifacts introduced by the presence of sodium hydroxide and heat. Moreover, the effective density differentiation of the product mixture of more-than-six similar products and reactants results in a long holdup time in the process cycle. The formation of mono-, di-, tri- and polyester cannot be selectively controlled, there is therefore a stockpile of "over esterified" polyols formed in the process.

It is a principal object of the present invention to provide a solvent-free trans-acidolysis process for preparing surface-active carbohydrate fatty-acid esters, which obviates the above drawbacks and/or limitations by adding no solvent during reaction, driving esterification rapidly to polyester formation and, when necessary, partially deacylate to form target products.

SUMMARY OF THE INVENTION

Accordingly, the present invention provides a trans-acidolysis process for preparing surface-active carbohydrate fatty-acid esters, comprising a low temperature, trans-acidolysis reaction between carbohydrate ester of low molecular-weight carboxylic acid (C2 or C3) and free fatty acid (C6 to C22) under reduced pressure and in the presence of an acid catalyst.

In one aspect the invention provides a solvent-free trans-acidolysis process for preparing surface-active carbohydrate fatty-acid esters comprising the steps of:

(a) reacting acylated carbohydrate with free fatty acid in the presence of an acid catalyst, under reduced pressure;

(b) decolorizing and extracting or crystallizing out the unreacted fatty acid, from the reaction mixture obtained in step (a), for recycle;

(c) precipitating out the unreacted acylated carbohydrate from the reaction mixture obtained in step (a), for recycle; and (d) recovering the carbohydrate fatty-ester layer, It is preferable that the reaction in step (a) is carried out with no solvent added to the reaction mixture. The reaction is preferably performed at a temperature range of 60 to 95 degree C. The precipitation of the unreacted acylated carbohydrate in step (c) may be achieved by cooling the carbohydrate fatty acid ester layer to a temperature between −4 and 10 degree C.

By providing a trans-acidolysis process for preparing surface-active carbohydrate fatty-acid esters in accordance with the invention mono-, di- and poly-fatty esters of C2 or C3-acylated carbohydrates, with HLB values of 1 to 10, may be obtained depending on the degree of substitution and chain-length of the fatty acid moiety.

In a further aspect of the invention, carbohydrate fatty esters with free hydroxyl groups of HLB values 8–16 may be obtained by a further step of partial hydrolysis in the presence of an acid catalyst.

In a further aspect of the invention, the unreacted free fatty acids and the unreacted carbohydrate esters of low molecular-weight carboxylic acids are removed during purification, and recycled to the starting reactant mixture.

The advantages of the process in accordance with the present invention, which circumvent at least one of the above limitations of the prior art, are:

(1) avoiding solvent as a reaction medium. The C2- or C3-acyl group attached to the reactant carbohydrate is a good protecting and leaving group and, at the same time, enhances the solubility of the carbohydrate moiety in the fatty acid;

(2) using low pressure to drive the reaction equilibrium forward at a reduced energy demand. This results in high yield (>90%), less isomerization and degradation of products.

(3) The feedstock is renewable natural resources, readily available and cheap. Unreacted substrates are recycled. This process is thus commercially viable.

(4) The invention is applicable to both batch-wise and continuous carbohydrate fatty ester processes.

(5) High-grade (98% pure) carbohydrate fatty acid esters can be obtained.

(6) This process is adaptable for producing a number carbohydrate fatty acid esters.

Without limiting the scope of the invention, other objects and advantages of the invention will become apparent upon reading the following detailed description and accompanying drawings.

BRIEF DESCRIPTION OF THE DRAWINGS

The invention may be better understood by reference to the drawings wherein.

DETAILED DESCRIPTION OF THE INVENTION

In accordance with the process for preparing carbohydrate fatty-acid esters of the present invention, the preferred reactant C2- or C3-acylated carbohydrates includes mono to trisaccharide carbohydrates, and the preferred free fatty acids includes C6–C22 chain-length, with zero, mono or di-unsaturations.

In the present process, the acid catalysts includes concentrated sulphuric acid and camphorsulfonic acid, in the case of the monosaccharides; and boron trifluoride diethyl etherate, alkyl sulphonic acid polysiloxanes and tosylic acid, in the case of the di- and tri-saccharides.

The carbohydrate fatty ester of the present process has the following chemical structures:

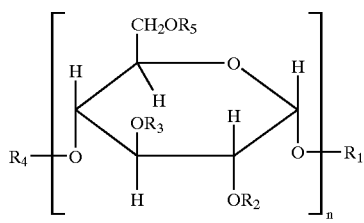

wherein R2, R3, R5 are each selected from the group consisting of H, $CH_3CO$, $CH_3CH_2CO$, and C6–C22 fatty acyl group; R1, and R4 are each selected from the group consisting of a partially or peracylated mono- or di-saccharide, H, $CH_3CO$, $CH_3CH_2CO$ or C6–C22 fatty acyl group; and n is an integer with value equal to 1, 2, or 3; wherein the primary monosaccharide unit could be a furanosyl, pyranosyl or a C2–C6 open-chain structure.

Step 1

Figure 1:
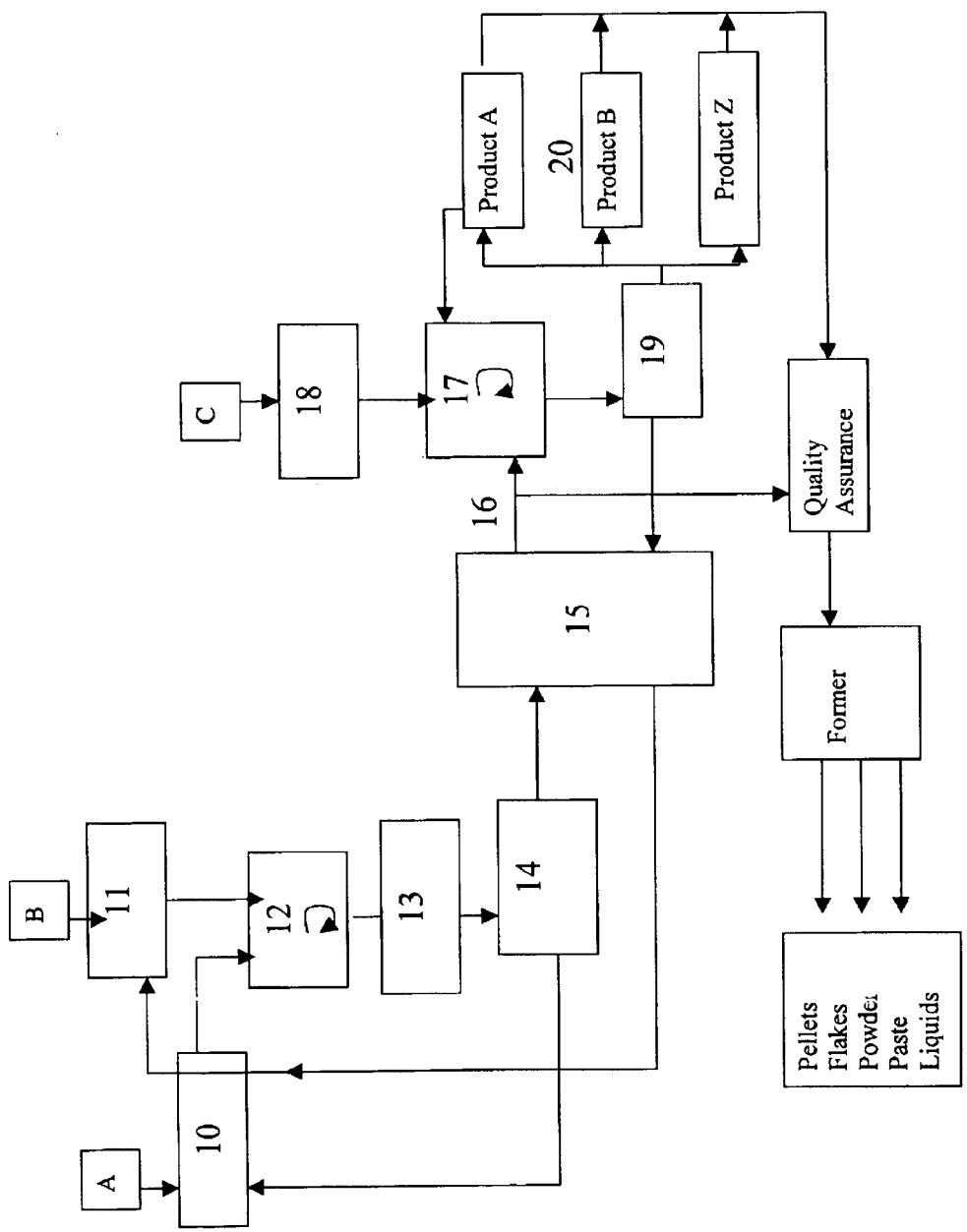
FIG. 1 is a process flow diagram of a preferred embodiment of the present invention.

Referring to FIG. 1, a C2- or C3-acylated carbohydrate 10, (preferably, mono to tri-saccharide) is reacted with a C6–C22 free fatty acid, 11, in reactor 12. The reaction is carried out in the presence of an acid catalyst, with continuous stirring at a temperature range from 60 to 95 degree C. (preferably from 80 to 90 degree C. for the monosaccharides and 60 to 75 degree C. for the di- and trisacchrides), under reduced pressure ranging from 4 to 20 Torr, (preferably from 5 to 10 Torr) and, without adding any solvent.

The reaction is continued for 3–6 hours after which it is then stopped and the reaction mixture is then taken up in an organic solvent such as iso-propanol, n-propanol, ethyl acetate or ethanol.

The low molecular weight C2- or C3-carboxylic acid, which is a by-product of the trans-acidolysis, is trapped by condensation and kept for other uses.

Step 2

The reaction mixture is then passed onto a decoloriser 13 where it is decolorized by contact with an adsorbent, such as activated carbon, and then filtered.

The unreacted free fatty acid and the unreacted acylated carbohydrate may then be recovered and recycled back as streams 11 and 10 respectively by either step 3 or step 4 as described below:

Step 3

The solvent in step 2 is removed by vacuum distillation, in distiller 15, at temperature between 30 and 50 degree C. and the unreacted fatty acid is then extracted with hexane. Hexane is then vacuum distilled, at temperature between 30 and 50 degree C., to recover the unreacted fatty acid. The remaining reaction mixture is redissolved in the solvent used in Step 2 to form 30–40% w/v solution and cool to −4 to 10 degree C. in the chiller separator 14 to give unreacted acylated carbohydrate precipitate. The filtrate solvent is then vacuum distilled off to give product acylated carbohydrate fatty esters 16. The recovered unreacted fatty acid and acylated carbohydrate are kept for recycle back as streams 11 and 10 respectively into reactor 12.

Step 4

As an alternatively to Step 3, the unreacted fatty acid is crystallized out by spiking the solvent in step 2 with 10–20% V/V water and cooling the solution to between 8 to 12 degree C. in the chiller separator 14. The unreacted acylated carbohydrate is then removed as precipitate by cooling the solution further to between −4 and 0 degree C. The filtrate solvent is then vacuum distilled off to give product acylated carbohydrate fatty esters 16. The recovered unreacted fatty acid and acylated carbohydrate are kept for recycle into reactor 12.

Step 5

In order to modify the HLB profile of the product to a desirable level, the product acylated carbohydrate fatty ester 16 obtained in Step 3 or 4 may be passed onto a second reactor 17, wherein free hydroxyl groups are librated by partial hydrolysis in the presence of an acid catalyst, 18 to produce the required HLB profile depending on the degree of substitution, deacylation and chain length of the fatty acyl group. Details of the HLB profile of products, covering 1 to 16 are given in FIG. 2.

The free fatty acid, which may be librated during hydrolysis, is removed by crystallization in the chiller separator 19 and recycled to reactor 12.

Figure 2:
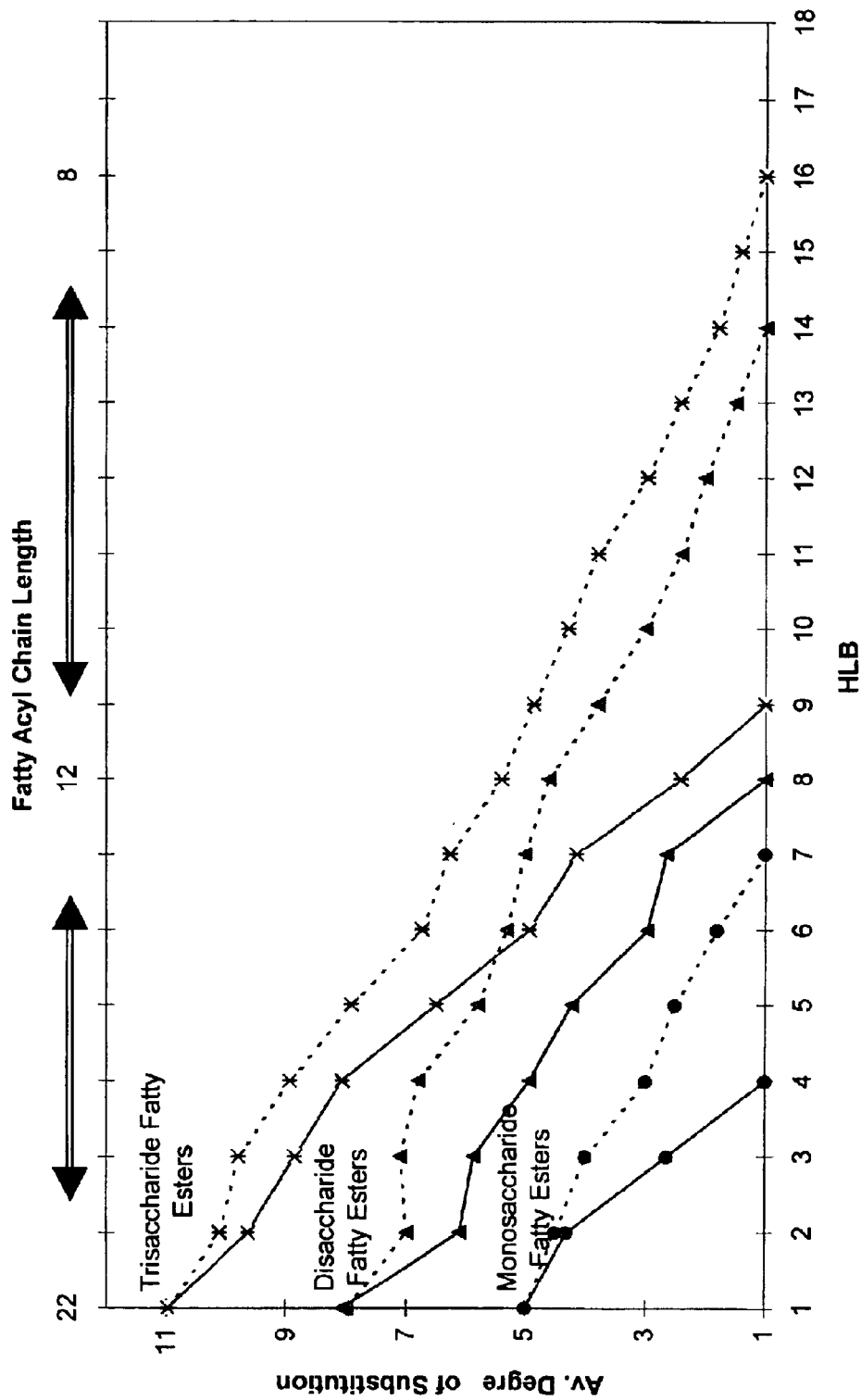
FIG. 2 is a graph of HLB profiles of product carbohydrate fatty acid esters before and after deacylation.

By varying the degree of deacylation and fatty acyl chain length in the carbohydrate fatty acid esters, products having distinct HLB values of 1 to 16 may be produced, as detailed in FIG. 2. These products have varying solubilities and sublimation temperatures and are thus separated into carbohydrate fatty acid esters by staged cooling between the temperatures of 10 and −15 degree C., depending on the esters present, at 20.

Stage 6

After the product separation by staged cooling at 20, the product may then be passed through quality assurance and onto the former to give the desired form such as pellets, flakes, powder, paste or liquid for supply to downstream users.

The following examples will further illustrate the present invention.

EXAMPLE 1

Preparation of Acetylated Glucose Laurate and the Partially Deacylated Glucose Laurate a) Preparation of Acetylated Glucose Laurate.

0.03 mol (6.00 g) of lauric acid (Fluka Chemika, Switzerland) was added into a three-necked, round-bottom flask equipped with a magnetic stirrer, stopcocks, a vacuum take-off line leading to a liquid nitrogen cold-trap and a vacuum pump. 0.01 mol (3.90 g) of Glucose pentaacetate, GPA, (Fluka Chemika, Switzerland) was added and the mixture was heated to 80–100 degree C. in an oil bath with continuous stirring until a homogenous solution was formed. 0.1% w/w (0.01 g) of concentrated sulphuric acid (or 0.2% camphorsulfonic acid) was then added and 5–10 Torr pressure was applied. The reaction was continued for 3 to 6 hours. The reaction was then stopped and taken up with 100 ml of n-propanol. The solution was then neutralized with aqueous 1M $NaHCO_3$, decolourised with 1.0 g activated charcoal and filtered warm. N-propanol was then removed by vacuum distillation.

Unreacted lauric acid was extracted with 50×4 ml hexane. Hexane was vacuum distilled to recover unreacted lauric acid and kept for recycle. The glucose fatty ester was redissolved in warm n-propanol to form 30–40% w/v solution, cool to −4 to 0 degree C. and filtered to give unreacted GPA as precipitate. The filtrate n-propanol was then vacuum distilled off to give 70–85% pure acetylated glucose laurate. Repeated fatty acid extraction and GPA precipitation gave 90–95% pure product (90.2% yield). Details of the HLB profile of products is given in FIG. 2 which shows Hydrophile-Lipophile-Balance (HLB) Profiles of Product Carbohydrate Fatty Acid Esters before (solid lines) and after (dotted lines) deacylations.

KEY: ◦=mono-, Δ=di- and *=tri-saccharide fatty acid ester.

Alternatively, in a reaction not shown in FIG. 1, unreacted fatty acid is crystallized out by spiking the n-propanol solution with 10–20% V/V water and cooling the solution to between 8 to 12 degree C., and then removing the unreacted GPA as precipitate by cooling the solution further to between −4 and 0 degree C.

Either method of extracting the fatty acid may be used depending on convenience and choice of facility.

b) Partial Deacylation of Acetylated Glucose Laurate

A portion of acetylated glucose laurate obtained above was added to $CF_3COOH:H_2O$ (7:3) to form a 20–50% w/v solution and agitated for a duration of time between 15 minutes to 2 hours, at room temperature (22–33 degree C.). Partially deacylated glucose fatty esters of various HLB values, depending on the duration of treatment, fatty acyl chain length and degree of substitution, as detailed in FIG. 2, was obtained. The solvent was distilled off under reduced pressure. The product is separated into carbohydrate fatty acid esters of varying degree of deacylation and or substitution by staged cooling between the temperatures of 10 and −15 degree C.

EXAMPLE 2

Preparation of Acetylated Sucrose Oleate and the Partially Deacylated Sucrose Oleate a) Preparation of Acetylated Sucrose Oleate.

0.06 mol (16.93 g) of oleic acid (Fluka Chemika, Switzerland) was weighed into a three-necked, round-bottom flask equipped with a magnetic stirrer, stopcocks, a vacuum take-off line leading to a liquid nitrogen cold-trap and a vacuum pump. 0.01 mol (6.79 g) of sucrose octaacetate, SOA, (Fluka Chemika, Switzerland) was added and the mixture was heated to 80–95 degree C. in an oil bath with continuous stirring until a homogenous solution was formed. 0.01% w/w tosylic acid (or alkyl sulfonic acid polysiloxane, or $BF_3.OEt_2$) was then added. Reaction temperature was then reduced to between 60–75 degree C. and 5–10 Torr pressure was applied. The reaction was continued for 3 to 6 hours. The product was taken up in 250 ml of iso-propanol, neutralized with aqueous 1M $NaHCO_3$, decolourised with 2.0 g activated charcoal, and filtered. Iso-propanol was then removed by vacuum distillation. Unreacted oleic acid was extracted with 50×4 ml hexane and kept for reuse. The sucrose fatty ester was redissolved in warm iso-propanol to form 30–40% w/v solution, cool to −4 to 0 degree C. and filtered to give unreacted SOA as precipitate. The filtrate iso-propanol was then distilled off to give 70–85% pure acetylated sucrose oleate. Repeated hexane extraction and SOA precipitation gave 90–95% pure product (87% yield).

b) Partial Deacylation of Acetylated Sucrose Oleate

A portion of acetylated sucrose oleate obtained above was added to $CF_3COOH:H_2O$ (7:3) to form 20–50% w/v solution and agitated for a duration of time between 15 minutes to 2 hours, at room temperature (22–33 degree C.). Partially deacylated sucrose fatty esters of various HLB values, depending on the duration of treatment, fatty acyl chain length and degree of substitution, as detailed in FIG. 2, was obtained. The solvent was distilled off under reduced pressure. If desirable, the product is separated into carbohydrate fatty acid esters of varying degree of deacylation and or substitution by staged cooling between the temperatures of 10 and −15 degree C.

EXAMPLE 3

Preparation of Acetylated Raffinose Laurate and the Partially Deacylated Raffinose Laurate a) Preparation of Raffinose Peracetate (RA)

Anhydrous raffinose (252 g, 0.50 mol) was added to 60 g anhydrous sodium acetate and stirred in 800 mL of acetic anhydride previously equilibrated to 100 degree C. Complete homogeneous solution is obtained in 30–50 minutes. The reaction is left to continue for 1–2 hours, after which the reaction mixture was poured into 4 liters of ice and left to stand for 2 hours. The raffinose peracetate precipitate formed is separated from the supernatant solution, redissolved in dichloromethane and washed three times with saturated sodium bicarbonate solution at neutral pH. The dichloromethane solution was then decolorized with 2.0 g activated charcoal and vacuum dried to give 492 g (90% yield) of raffinose peracetate white powder.

b) Preparation of Acetylated Raffinose Laurate.

0.06 mol (12.0 g) of lauric acid (Fluka Chemika, Switzerland) was weighed into a three-necked, round-bottom flask equipped with a magnetic stirrer, stopcocks, a vacuum take-off line leading to a liquid nitrogen cold-trap and a vacuum pump. 0.01 mol (11.54 g) of raffinose peracetate, RA (prepared above) was added and the mixture was heated to 80–100 degree C. in an oil bath with continuous stirring until a homogenous solution was formed. 0.01% w/w $BF_3.OEt_2$ (or tosylic acid or alkyl sulfonic acid polysiloxane) was then added. Reaction temperature was reduced to between 60and 75 degree C. and 5–10 Torr pressure was applied. The reaction was continued for 2 to 6 hours. The product was taken up in 250 ml of ethyl acetate, quenched with aqueous 1M $NaHCO_3$, decolourised with 2.0 g activated charcoal, and filtered. Ethyl acetate was then removed by vacuum distillation.

Unreacted lauric acid was extracted with 50×4 ml hexane and kept for reuse. The raffinose fatty ester was redissolved in warm iso-propanol to form 30–40% w/v solution, cool to between −4 and 0 degree C., and filtered to give unreacted RA as precipitate. The filtrate iso-propanol was then distilled off to give 70–85% pure acetylated raffinose laurate. Repeated hexane extraction and RA precipitation gave 90–95% pure product (85% yield).

c) Partial Deacylation of Acetylated Raffinose Laurate

A portion of acetylated raffinose laurate obtained above was added to $CF_3COOH:H_2O$ (7:3) to form 20–50% w/v solution and agitated for a duration of time between 15 minutes to 2 hours, at room temperature (22–33 degree C.). Partially deacylated raffinose laurate of various HLB values, depending on the duration of treatment, fatty acyl chain length and degree of substitution, as detailed in FIG. 2, was obtained. The solvent was distilled off under reduced pressure. The product is separated into carbohydrate fatty acid esters of varying degree of deacylation and or substitution by staged cooling between the temperatures of 10 and −15 degree C.

While the invention has been described with respect to preferred embodiment, it will be apparent to those skilled in the art that modifications and improvements may be made to the invention without departing from the spirit and scope of the invention. Therefore, the invention is not to be limited by the specific illustrative embodiment, but only by the scope of the appended claims.

What is claimed is:

1. A process for preparing carbohydrate fatty-acid esters comprising the steps of:
   (a) reacting, by solvent free trans-acidolysis, acylated carbohydrate with free fatty acid in the presence of an acid catalyst, under reduced pressure in the range of about 4–20 Torr;
   (b) decolorizing and separating out the unreacted fatty acid, from the reaction mixture obtained in step (a);
   (c) precipitating out the unreacted acylated carbohydrate from the reaction mixture obtained in step (b);
   (d) recovering carbohydrate fatty ester from the reaction mixture obtained in step (C); and
   (e) librating free hydroxyl groups by partial hydrolysis of the C2- or C3-acylated carbohydrate fatty acid ester in the presence of an acid catalyst to obtain carbohydrate fatty acid ester having free hydroxyl groups with Hydrophile-Lipophile-Balance (HLB) values of 1 to 16.

2. The process of preparing carbohydrate fatty-acid esters of claim 1, wherein in step (a), no solvent is added thereto.

3. The process of preparing carbohydrate fatty-acid esters of claim 1, wherein in the unreacted fatty-acid in the reaction mixture in step (b) is removed by precipitation from a solvent mixture at controlled temperature.

4. The process of preparing carbohydrate fatty-acid esters of claim 1, wherein the unreacted fatty-acid in the reaction mixture in step (b) is removed from the reaction mixture by solvent extraction.

5. The process of preparing carbohydrate fatty acid ester of claim 1 wherein the unreacted acylated carbohydrate is precipitated out in step (c) by cooling the reaction mixture in step (b) to a temperature in the range of −4 to 10 degree C.

6. The process of preparing carbohydrate fatty acid esters of claim 1, wherein the unreacted free fatty acids and the unreacted C2 or C3-acylated carbohydrate esters which are removed during purification steps (b) and (c) are recycled to the reactant mixture.

7. The process of preparing carbohydrate fatty-acid ester of claim 1 wherein step (a) is carried out at a pressure in the range of 5–10 Torr.

8. The process of preparing carbohydrate fatty-acid esters of claim 1, wherein mono-, di- and poly-fatty acid esters of C2- or C3-acylated carbohydrates of various Hydrophile-Lipophile-Balance (HLB) values are obtained.

9. The process of preparing carbohydrate fatty-acid esters of claim 1, wherein step (a) is processed at a temperature ranging from about 60 to about 95 degree C.

10. A process of preparing carbohydrate fatty acid esters comprising the steps of:
    (a) reacting, by solvent-free trans-acidolysis, acylated carbohydrate with free fatty acid in the presence of an acid catalyst, under reduced pressure in the range of about 4 –20 Torr;
    (b) decolorizing and separating out the unreacted fatty acid, from the reaction mixture obtained in step (a);
    (c) precipitating out the unreacted acylated carbohydrate from the reaction mixture obtained in step (b);
    (d) removing the unreacted free fatty acids and carbohydrate esters of low molecular-weight carboxylic acids during purification, and recycling the removed unreacted free fatty acids and carbohydrate esters to the starting reactant mixture; and
    (e) librating free hydroxyl groups by partial hydrolysis of the acylated carbohydrate fatty acid ester in the presence of an acid catalyst to obtain carbohydrate fatty acid ester having free hydroxyl groups with Hydrophile-Lipophile-Balance (HLB) values of 1 to 16.

11. The process according to claim 1 or 10 wherein the reactant carbohydrates include the group consisting of partially or peracylated mono-, di- and tri-saccharides in which the monosaccharide unit(s) is selected from the group consisting of furanosyl, pyranosyl or a C2–C6 open-chain structure.

12. The process according to claim 1 or 10 wherein the acyl group in the reactant acylated carbohydrates is acetic or propanoic acyl group.

13. The process according to claim 1 or 10 wherein, the acid catalysts includes sulphuric or camphorsulfonic acid, in the case of the monosaccharides; and boron trifluoride diethyl etherate, alkyl sulphonic acid polysiloxanes or tosylic acid, in the case of the di- and tri-saccharides.

14. The process according to claim 1 or 10 wherein the step (b) solvents are used to remove the unreacted fatty acid from the reaction mixture, said solvents selected from the group consisting of water, ethanol, iso-propanol, n-propanol ethyl acetate, and mixtures thereof.

15. The process according to claim 4 wherein the extraction solvent is hexane.

16. The process according to claim 1 or 10 wherein the free fatty acids have C6–C22 chain-length, with zero, mono or di-unsaturations.

17. The process according to claim 1 or 10 wherein the hydrolysis acid catalyst is trifluoroacetic acid.

18. The process according to claim 1 or 10 wherein the partially hydrolysed carbohydrate fatty acid esters are further separated by stage cooling, at controlled temperature ranging from about -15 to about 10 degree C, according to their degree og acylation.

* * * * *